United States Patent
Inglese et al.

(10) Patent No.: US 10,039,441 B2
(45) Date of Patent: Aug. 7, 2018

(54) DIGITAL DETECTOR

(75) Inventors: Jean Marc Inglese, Bussy-Saint-Georges (FR); Sylvie M. Bothorel, Paris (FR); Donna K. Rankin-Parobek, Honeoye Falls, NY (US)

(73) Assignee: Trophy, Marne la Vallee (FR)

( * ) Notice: Subject to any disclaimer, the term of this patent is extended or adjusted under 35 U.S.C. 154(b) by 476 days.

(21) Appl. No.: 13/996,324

(22) PCT Filed: Dec. 21, 2011

(86) PCT No.: PCT/US2011/066432
§ 371 (c)(1),
(2), (4) Date: Jul. 18, 2013

(87) PCT Pub. No.: WO2012/088243
PCT Pub. Date: Jun. 28, 2012

(65) Prior Publication Data
US 2013/0307923 A1    Nov. 21, 2013

Related U.S. Application Data

(60) Provisional application No. 61/425,867, filed on Dec. 22, 2010.

(51) Int. Cl.
*A61B 1/24* (2006.01)
*A61B 6/02* (2006.01)
(Continued)

(52) U.S. Cl.
CPC .............. *A61B 1/24* (2013.01); *A61B 6/025* (2013.01); *A61B 6/027* (2013.01); *A61B 6/032* (2013.01);
(Continued)

(58) Field of Classification Search
CPC .. G01T 1/00; A61B 1/24; A61B 6/025; A61B 6/032; A61B 6/14; A61B 6/145; A61B 6/4241; A61B 6/482
See application file for complete search history.

(56) References Cited

U.S. PATENT DOCUMENTS 4,176,278 A * 11/1979 Cushman ............... A61B 6/145
378/119
5,263,494 A    11/1993 Margelos et al.
(Continued)

FOREIGN PATENT DOCUMENTS

EP    0 534 548 A1    9/1992
JP    H07-275239    10/1995
(Continued)

OTHER PUBLICATIONS

International Search Report, Completed Jun. 21, 2012 for International Application No. PCT/US11/66432, 3 pages.
(Continued)

*Primary Examiner* — Peter D Le

(57) ABSTRACT

An extra-oral dental imaging apparatus for obtaining an image from a patient has a radiation source and a digital imaging sensor that provides, for each of a number of image pixels, at least a first digital value according to a count of received photons that exceed at least a first energy threshold. A mount supports the radiation source and the digital imaging sensor on opposite sides of the patient's head. There can be a computer in signal communication with the digital imaging sensor for acquiring one or more two-dimensional images.

17 Claims, 20 Drawing Sheets

(51) Int. Cl.
   *A61B 6/03* (2006.01)
   *A61B 6/14* (2006.01)
   *A61B 6/00* (2006.01)
   *H04N 5/232* (2006.01)
   *H04N 5/32* (2006.01)

(52) U.S. Cl.
   CPC .............. *A61B 6/14* (2013.01); *A61B 6/145* (2013.01); *A61B 6/4241* (2013.01); *A61B 6/4452* (2013.01); *A61B 6/482* (2013.01); *H04N 5/23238* (2013.01); *H04N 5/32* (2013.01)

(56) References Cited

U.S. PATENT DOCUMENTS

| | | | | |
|---|---|---|---|---|
| 5,579,361 | A | * | 11/1996 | Augais ............... A61B 6/14 348/E3.018 |
| 5,677,940 | A | | 10/1997 | Suzuki et al. |
| 5,995,583 | A | * | 11/1999 | Schick ............... A61C 9/0073 378/191 |
| 6,052,428 | A | * | 4/2000 | Nakano .............. A61B 6/4441 378/197 |
| 6,093,019 | A | * | 7/2000 | Morandi ............ A61C 13/0004 433/29 |
| 6,118,842 | A | | 9/2000 | Arai et al. |
| 6,289,074 | B1 | * | 9/2001 | Arai .................... A61B 6/14 378/38 |
| 6,408,050 | B1 | * | 6/2002 | Han .................... G01T 1/17 378/98.11 |
| 6,414,708 | B1 | * | 7/2002 | Carmeli ............. A61B 1/00045 348/42 |
| 6,493,415 | B1 | * | 12/2002 | Arai .................... A61B 6/14 378/38 |
| 6,594,539 | B1 | * | 7/2003 | Geng .................. A61B 1/247 264/16 |
| 7,646,845 | B2 | | 1/2010 | Lecomte et al. |
| 7,780,350 | B2 | | 8/2010 | Tranchant |
| 2001/0010538 | A1 | * | 8/2001 | Ooshima ............ A61B 1/24 348/66 |
| 2002/0030661 | A1 | * | 3/2002 | Gemunder .......... A61B 1/00039 345/156 |
| 2002/0034277 | A1 | | 3/2002 | Laner |
| 2002/0067407 | A1 | * | 6/2002 | Cooper ............... A61B 6/14 348/66 |
| 2003/0235265 | A1 | | 12/2003 | Clinthorne et al. |
| 2006/0040230 | A1 | * | 2/2006 | Blanding ............ G01J 3/02 433/26 |
| 2008/0298554 | A1 | | 12/2008 | Tacconi et al. |
| 2008/0317200 | A1 | | 12/2008 | Lecomte |
| 2009/0039273 | A1 | * | 2/2009 | Tkaczyk ............. G01T 1/171 250/370.06 |
| 2009/0076321 | A1 | * | 3/2009 | Suyama ............. A61B 1/00041 600/109 |
| 2009/0124882 | A1 | | 5/2009 | Massie et al. |
| 2009/0232275 | A1 | * | 9/2009 | Spartiotis .......... A61B 6/14 378/40 |
| 2010/0034340 | A1 | | 2/2010 | Spartiotis et al. |
| 2010/0172462 | A1 | | 7/2010 | Tancredi et al. |
| 2010/0278299 | A1 | | 11/2010 | Loustauneau |
| 2010/0303024 | A1 | | 12/2010 | Gossain |
| 2012/0039436 | A1 | | 2/2012 | Bothorel et al. |
| 2013/0307923 | A1 | | 11/2013 | Inglese et al. |

FOREIGN PATENT DOCUMENTS

| | | |
|---|---|---|
| JP | 2847655 B | 1/1999 |
| JP | 2006-187607 A | 7/2006 |
| JP | 2008-092990 | 4/2008 |
| JP | 2008-229322 | 10/2008 |
| JP | 2009-502227 A | 1/2009 |
| JP | 2011-085479 | 4/2011 |
| JP | 2013-524859 | 6/2013 |
| WO | 2010/128404 A1 | 11/2010 |
| WO | 2011/013771 A1 | 2/2011 |
| WO | WO 2012/086648 A | 6/2012 |
| WO | 2012/168756 A1 | 12/2012 |

OTHER PUBLICATIONS

International Search Report, Completed Feb. 1, 2013 for International Application No. PCT/US12/43510, 3 pages.
Supplementary European Search Report, Application No. EP12859406, dated Jun. 18, 2015, 2 pages.
EP Supplementary Partial Search Report, dated May 10, 2016, EP Application No. 11 85 1524, 3 pages.
Chinese Office Action from Chinese Patent Application No. 201180068293.1 dated Sep. 28, 2017, 25 pages.

* cited by examiner

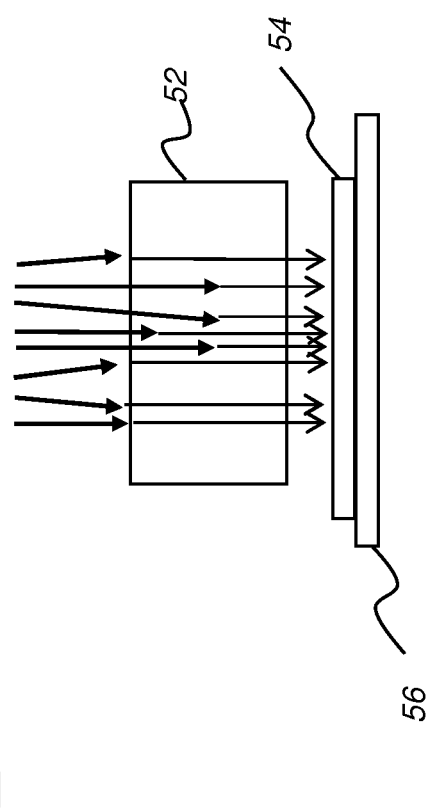

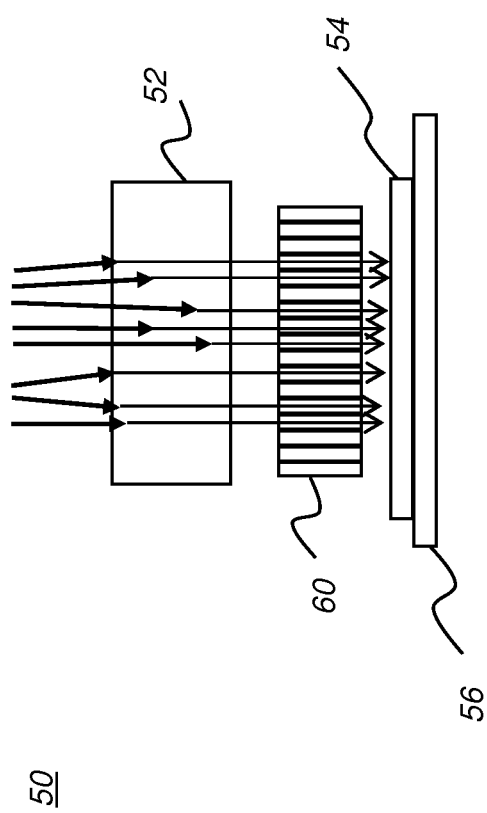

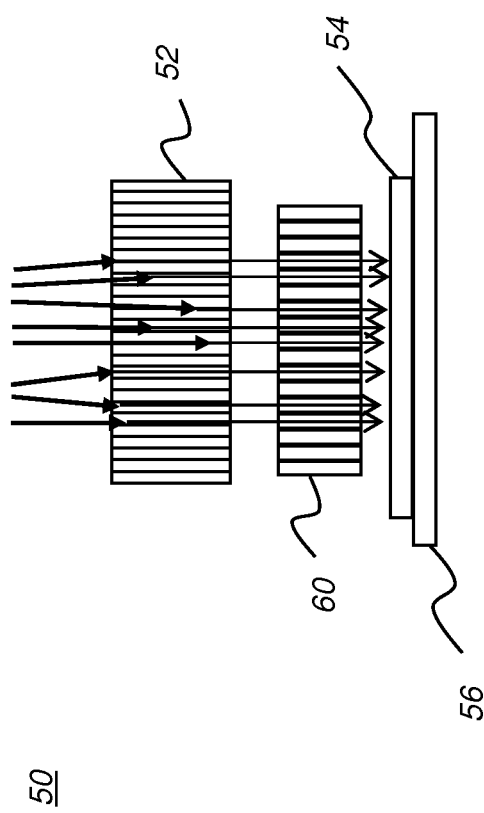

DIGITAL DETECTOR

CROSS REFERENCE TO RELATED APPLICATIONS

This application claims the benefit of and is a US national phase filing of PCT application No. PCT/US11/66432 filed Dec. 21, 2011 that is entitled "DIGITAL DETECTOR" in the names of Jean Marc Inglese, Sylvie Bothorel and Donna K. Rankin-Parobek, which claims benefit of Provisional application U.S. Ser. No. 61/425,867, provisionally filed on Dec. 22, 2010 that is entitled "DIGITAL DETECTOR" in the names of Jean Marc Inglese, Sylvie Bothorel and Donna K. Rankin-Parobek, and the disclosures of both priority applications are incorporated herein by reference in their entirety.

FIELD OF THE INVENTION

The invention relates generally to the field of dental imaging and more particularly to apparatus and methods for obtaining images from the head of a patient.

BACKGROUND OF THE INVENTION

A computerized tomography (CT) imaging apparatus operates by acquiring multiple 2D images with a rotating imaging ensemble or gantry that has an x-ray source and, opposite the x-ray source, an imaging sensor rotating about a fixed axis relative to the patient. CT imaging allows the reconstruction of 3D or volume images of anatomical structures of the patient and is acknowledged to be of particular value for obtaining useful information for assisting diagnosis and treatment.

There is considerable interest in the use of CT imaging in dental and ear-nose-throat (ENT) applications, as well as for other imaging of the patient's head. A number of volume imaging system designs have been proposed for this purpose. Among proposed solutions are hybrid systems that combine panoramic imaging and CT imaging. For example, U.S. Pat. No. 6,118,842 entitled "X-RAY IMAGING APPARATUS" to Arai et al. discloses an X-ray imaging apparatus that supports both imaging modes. The apparatus includes an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, only one large area X-ray detector is used. The X-ray imaging apparatus can obtain both types of images by switching modes during the imaging session. However, the proposed imaging apparatus requires an expensive detector capable of carrying out both imaging functions in a satisfactory manner. Additionally, systems of this type typically compromise image quality by using a uniform distance between the X-ray source and detector, even though different distances would be more advantageous.

By way of example, FIG. 1 shows an embodiment of a conventional CT imaging apparatus 40. A column 18 is adjustable for height of the subject. The patient 12 or other subject, shown in dotted outline, is positioned between an x-ray source 10 and an x-ray imaging sensor panel 20, also termed an imaging detector. X-ray imaging sensor panel 20 rotates on a rotatable mount 30 in order to position a CT sensor 21 for obtaining the exposure. CT sensor 21 is positioned behind the subject, relative to x-ray source 10. The operator rotates CT sensor 21 into this position as part of imaging setup. With rotation of mount 30, sensor 21 and source 10 revolve about the head of the patient, typically for some portion of a full revolution. Still other dental imaging system solutions combine CT, panoramic, and cephalometric imaging from a single apparatus. With such combined systems, the required amounts of radiation exposure can be a concern, particularly for CT imaging, which can require numerous images, each from a separate exposure.

Conventional digital radiography detectors have some limitations related to how attenuation of radiation energy at a single exposure is interpreted. For example, it can be very difficult, from a single exposure, to distinguish whether an imaged object has a given thickness or a given attenuation coefficient. To resolve this ambiguity, some systems provide separate, sequential low-energy and higher energy exposures and use the resulting difference in image information to distinguish between types of materials. However, in order to provide this information, this type of imaging requires that the patient be subjected to additional radiation for the second exposure. This problem can be compounded for CT imaging, in which multiple images are obtained, one from each of a number of angles of revolution about the patient.

Conventional CT imaging provides useful information that aids in diagnosis and treatment, but is constrained by limitations of the imaging sensor apparatus itself and by concerns over exposure levels needed for obtaining the desired image quality. Thus, it can be seen that there is a long-felt need for improved methods of imaging that can achieve high levels of image quality with reduced exposure and at more favorable cost for dental, ENT, and other imaging of the head.

SUMMARY OF THE INVENTION

Embodiments of the present invention address the need for advancing the imaging arts, particularly for imaging of the head. Embodiments of the present invention adapt photon-counting and related imaging solutions to the problem of imaging for dental, ENT, and related applications. Using embodiments of the present invention, a medical practitioner can obtain useful images for patient treatment, taking advantage of reduced exposure levels and other advantages that photon-counting solutions provide.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an extra-oral dental imaging apparatus for obtaining an image from a patient, the apparatus comprising a radiation source; a digital imaging sensor that provides, for each of a plurality of image pixels, at least a first digital value according to a count of received photons that exceeds at least a first energy threshold; a mount that supports the radiation source and the digital imaging sensor on opposite sides of the patient's head; and a computer in signal communication with the digital imaging sensor for acquiring one or more two-dimensional images.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A is a schematic view that shows a digital detector using a scintillator in conventional digital radiographic imaging.

FIG. 2C is a schematic view that shows a digital detector using a thicker scintillator with a fiber optic array in conventional digital radiographic imaging.

FIG. 2D is a schematic view that shows a digital detector using a structured scintillator with a fiber optic array in conventional digital radiographic imaging.

DESCRIPTION OF EXEMPLARY EMBODIMENTS

Figure 1:
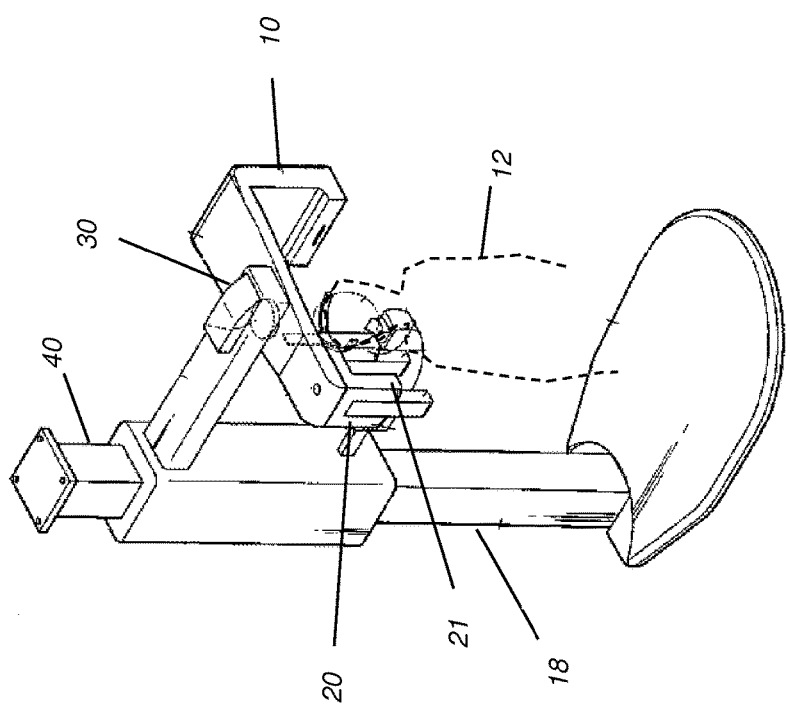
FIG. 1 shows a CT imaging apparatus for dental or ear-nose-throat (ENT) imaging.

The following is a description of the exemplary embodiments of the invention, reference being made to the drawings in which the same reference numerals identify the same elements of structure in each of the several figures.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D images of pixels, taken at different relative angles, then combining the image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

In the context of the present disclosure, the term "code value" refers to the value that is associated with each volume image data element or voxel in the reconstructed 3-D volume image. The code values for CT images are often, but not always, expressed in Hounsfield units (HU).

In the context of the present invention, the terms "digital sensor" and "digital detector" are considered to be equivalent. These describe the panel that obtains image data in a digital radiography system. The term "revolve" has its conventional meaning, to move in a curved path or orbit around a center point.

Figure 2B:
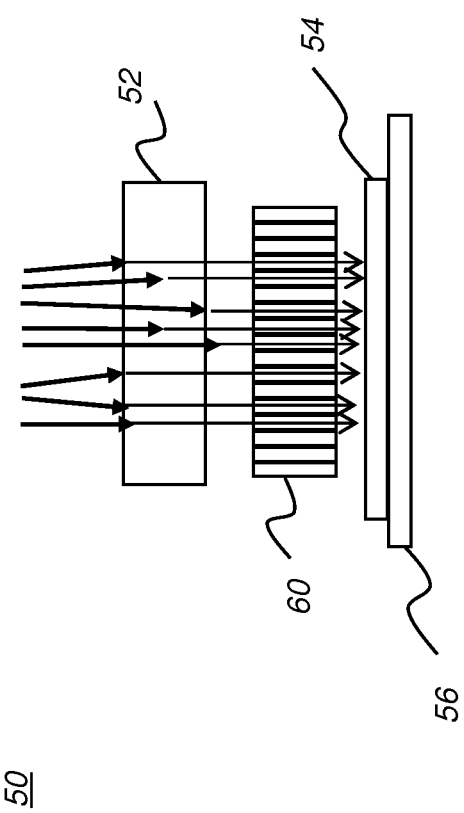
FIG. 2B is a schematic view that shows a digital detector using a scintillator with a fiber optic array in conventional digital radiographic imaging.

In order to more fully understand aspects of the present invention, it is instructive to consider different approaches used for imaging in conventional practice and to compare these with aspects of imaging according to embodiments of the present invention. FIGS. 2A through 2E schematically illustrate different approaches to radiologic imaging. FIG. 2A shows elements of an x-ray imaging sensor 50 that uses an indirect imaging method for generating image data in response to radiation through a patient or other subject. In this model, x-ray photons are incident on an x-ray converting element 52 that converts the energy from ionizing x-ray radiation to visible light or other light energy. X-ray converting element 52 is commonly referred to as a scintillator. An energy detecting element 54, mounted on a support structure 56, then detects the converted energy, such as using an array of photocells. The photocells can be light-sensitive CMOS (Complementary Metal-Oxide Semiconductor) components formed in an array as a semiconductor chip and providing a signal corresponding to each detected image pixel. Unconverted x-ray photons are trapped in an optical fiber plate.

Scatter, resulting in cross-talk between pixels and consequent loss of some amount of resolution, is one acknowledged problem with the basic approach shown in FIG. 2A. The modification of FIG. 2B addresses this problem and reduces the number of unconverted x-ray photons by adding a fiber-optic array 60 between the scintillator or x-ray converting element 52 and energy detecting elements 54. FIG. 2C shows another modification that can help to improve sensitivity to radiation, enlarging the width of the scintillator or x-ray converting element 52; however, this solution can result in some loss of sharpness in the obtained image.

FIG. 2D shows the use of a structured scintillator serving as x-ray converting element 52. The structured scintillator can use a material such as cesium iodide (CsI), although this material is structurally fragile, expensive and has some limitations with respect to image quality. Some believe that thicker layers of CsI attenuate light faster, such that they produce extra visible-light photons. This modified scintillator type can be used in addition to fiber-optic array 60 as shown in FIG. 2D for some improvement in performance.

The conventional model shown in FIG. 2A and improvements outlined with respect to FIGS. 2B, 2C, and 2D provide a reasonable level of imaging performance for dental imaging applications. However, even with the added cost and complexity of the additional components and features used, only incremental improvements in image quality and overall performance are achieved.

Figure 3:
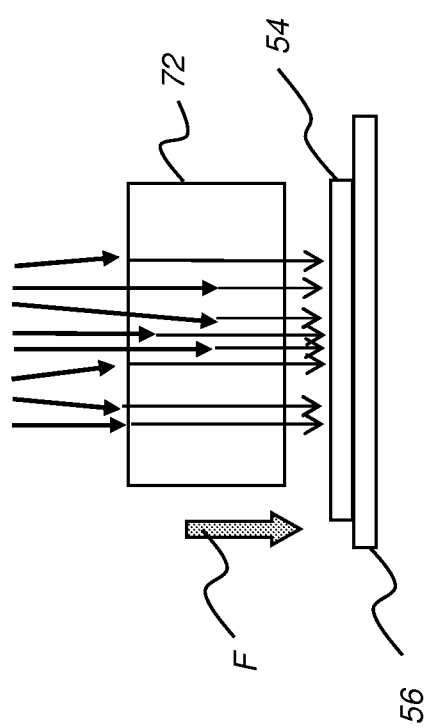
FIG. 3 is a schematic view that shows a digital detector using a photon counting for digital radiographic imaging.

An alternative approach to image capture using a direct imaging method is shown in FIG. 3. An imaging sensor 70 using direct detection has a direct detection element 72, such as a semiconductor or other sensitive material, that converts incident x-ray photons to an electron flow. The excited electrons are then accelerated by an electrical field F and sensed by an electron-sensitive CMOS array that acts as energy detecting element 54. The total energy of the cloud of electrons is representative of the energy of the incident x-ray photon. Advantageously, with direct detection imaging sensor 70, each incoming x-ray photon is much more likely to be detected than with indirect imaging devices. This increases the DQE (detective quantum efficiency), a performance metric for an imaging detector. Reduced scatter, a result of the electric field that guides electron charge toward the CMOS array elements, makes this approach more efficient, improves resolution, and provides a more favorable signal-to-noise (S/N) ratio. As a result, lower levels of ionizing radiation can be used for obtaining an image with direct detection imaging sensor 70 than are needed with the more conventional indirect devices described with reference to FIGS. 2A-2D.

Figure 15:
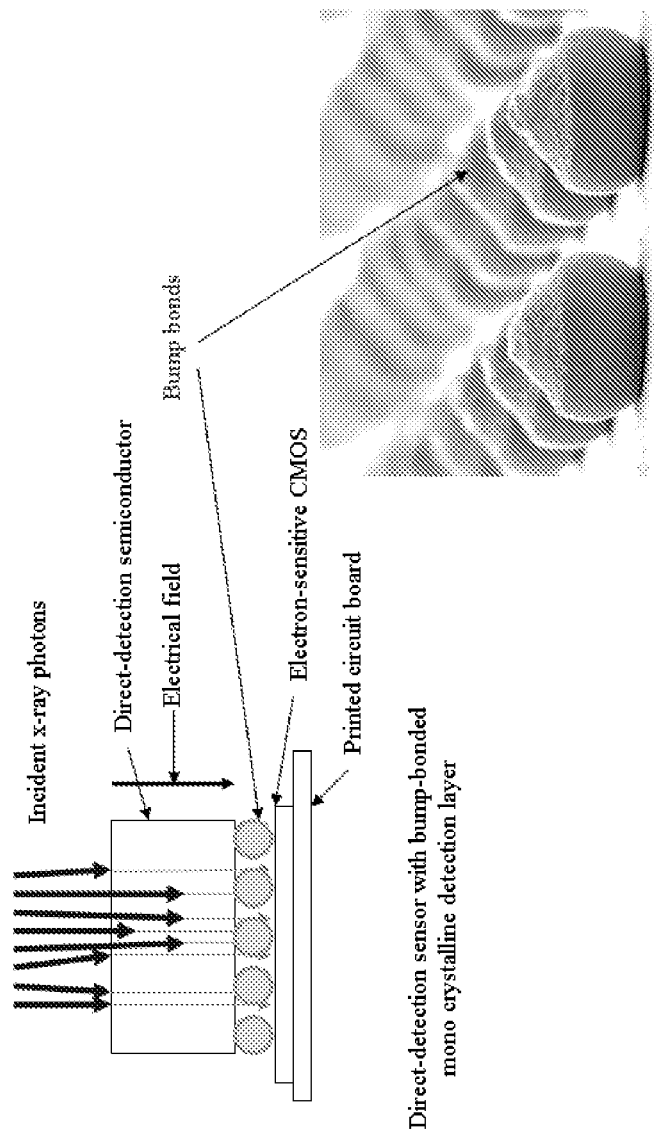
FIG. 15 is a diagram that shows monocrystals bump-bonded to silicon.
Figure 16:
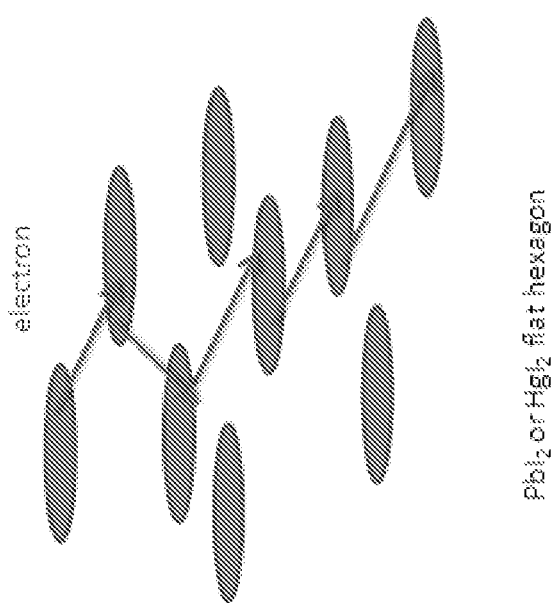
FIG. 16 is a diagram that shows polycrystal of PbI2 or HgI2

Direct-detection semiconductors used for direct detection element 72 can include polycrystalline or monocrystalline materials. Monocrystalline materials are advantaged over polycrystalline for ease of fabrication and handling; however, there are size constraints to detectors formed from monocrystalline materials. The organized structure of monocrystals guides the propagation of the electrons submitted to an electrical field. Monocrystals are connected to the electron-sensitive CMOS structure by bump bonds. FIG. 15 is a diagram that shows a direct-detection semiconductor bump-bonded to the electron-sensitive CMOS. Polycrystalline materials are more difficult to fabricate and handle, but are capable of providing larger detectors. Candidate materials for this purpose include cadmium telluride (CdTe or CadTel), lead iodide ($PbI_2$), lead oxide (PbO), and mercuric iodide ($HgI_2$), and types of poly crystal, amorphous Selenium (aSe) and other materials. Referring to FIG. 16, the random structure of polycrystals creates a scattering of the electrons submitted to an electrical field, resulting in a lack of sharpness of the resulting image. A polycrystal of $PbI_2$ or $HgI_2$ is in a form of hexagonal flat structures randomly disposed and the electrons go from one hexagon to another. Polycrystals can be directly coated on the silicon of the CMOS without the need of bump-bonds.

Figure 4:
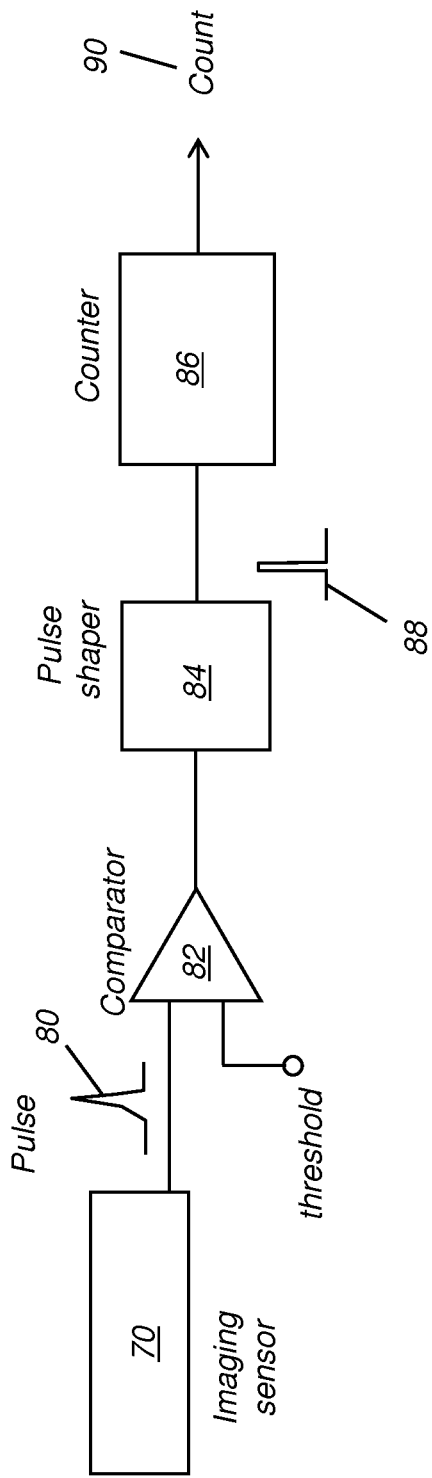
FIG. 4 is a schematic diagram that shows the image processing chain for each pixel of the digital detector when using photon counting.

Another distinction is made between how x-ray detectors record and report the received energy. Integrating x-ray sensors are spatially digitized and provide an analog output that represents the accumulated charge received for each pixel during the exposure. High noise levels can be a problem with integrating sensors. Another approach is commonly termed "photon-counting". In this alternative method, each incoming photon generates a charge, and each of these events is reported or counted. The actual count of photons, or a value computed according to the count, is provided as the image data for each pixel. Advantageously, photon counting has high immunity to noise, provided that pulse strength exceeds background noise levels. FIG. 4 shows the photon-counting sequence in schematic form. An incoming photon generates a pulse 80 at a given energy level. The pulse 80 energy is compared against a threshold value at a comparator 82 and shaped in a pulse shaper 84 to form a shaped pulse 88. A counter 86 then records the pulse event and provides a digital output, a pulse count value 90. A separate pulse count value 90 is obtained for each pixel element in imaging sensor 70. The threshold value can be adjustable or selectable from a range of values, depending on the photon energies of interest. Photon counting x-ray detectors provide suitable performance at low signal level, and therefore allow reducing the x-ray dose given to a patient.

Applicants have recognized that these detector technologies can be combined. For example, combining: (1) Indirect-Detection with Integration, (2) Direct-Detection with Integration, (3) Indirect-Detection with Photon-Counting, and (4) Direct-Detection with Photon-Counting. Indirect-Detection with Integration provides reduced detector cost and scalability. Direct-Detection with Integration provides reduced dose and large-scale detectors. Indirect-Detection with Photon-Counting provides for reduced dose. Direct-Detection with Photon-Counting can provide reduced dose and/or color x-ray.

A further advantage of pulse counting relates to its capability to count pulses 80 at multiple threshold values. Referring to the schematic diagram of FIG. 5, two comparators 82a and 82b are shown for measuring pulse energy. In this particular configuration, a comparator 82a, a pulse shaper 84a, and a counter 86a provide a count 90a value for all pulses above a first threshold; similarly, a comparator 82b, a pulse shaper 84b, and a counter 86b account for only pulses above a higher, second threshold and provide a count 90b accordingly. Simple subtraction then identifies the different power levels achieved for each pulse. It can be appreciated that more than two threshold levels can be measured, using a corresponding arrangement of comparator circuitry, allowing pulse counts at any of a number of threshold values. In addition, thresholds can be selectable, such as adjustable to adjust the response of imaging sensor 70 to various photon energy levels. Thus, for example, an operator can use a set of preset thresholds for differentiating softer from denser tissue in the image that is finally generated.

In addition to setting minimum thresholds, embodiments of the present invention also provide the option of using upper or maximum thresholds for photon energy. This capability can be used for a number of functions, including reducing the generation of excessive noise signals such as from metal artifacts or x-rays passing directly through the direct detection material.

Figure 5:
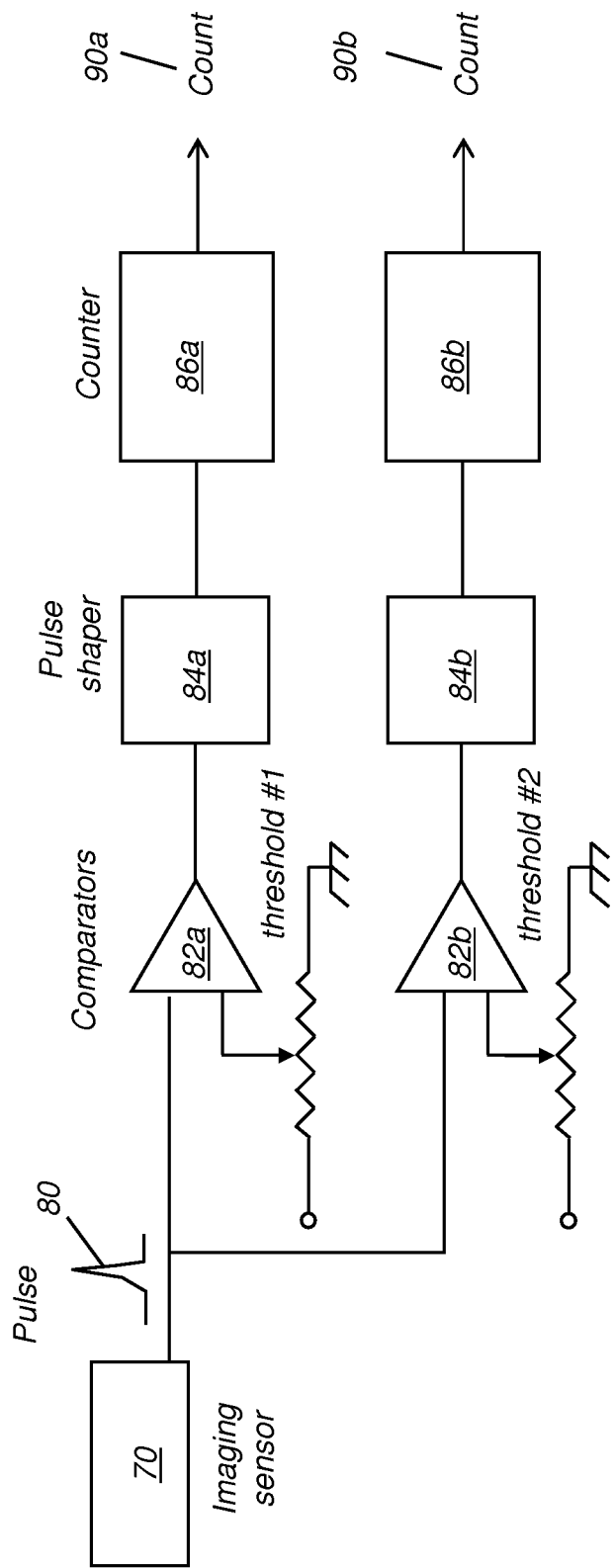
FIG. 5 is a schematic diagram that shows the image processing chain for each pixel of the digital detector using multiple thresholds when using photon counting.
Figure 6A:
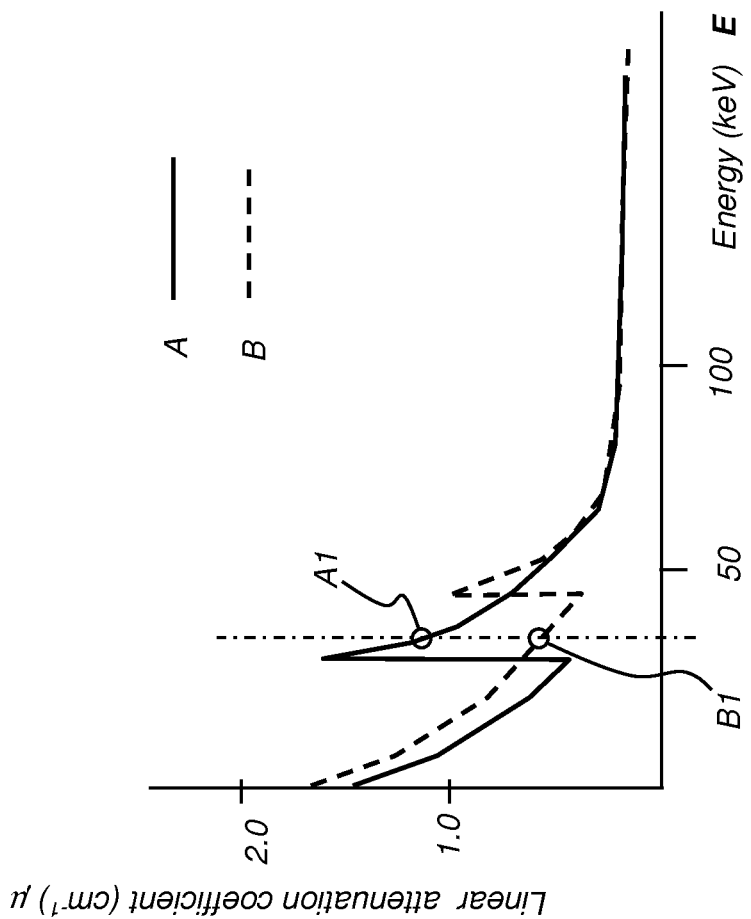
FIG. 6A is a graph that shows linear attenuation characteristics at different energy levels for two exemplary metallic materials.
Figure 6B:
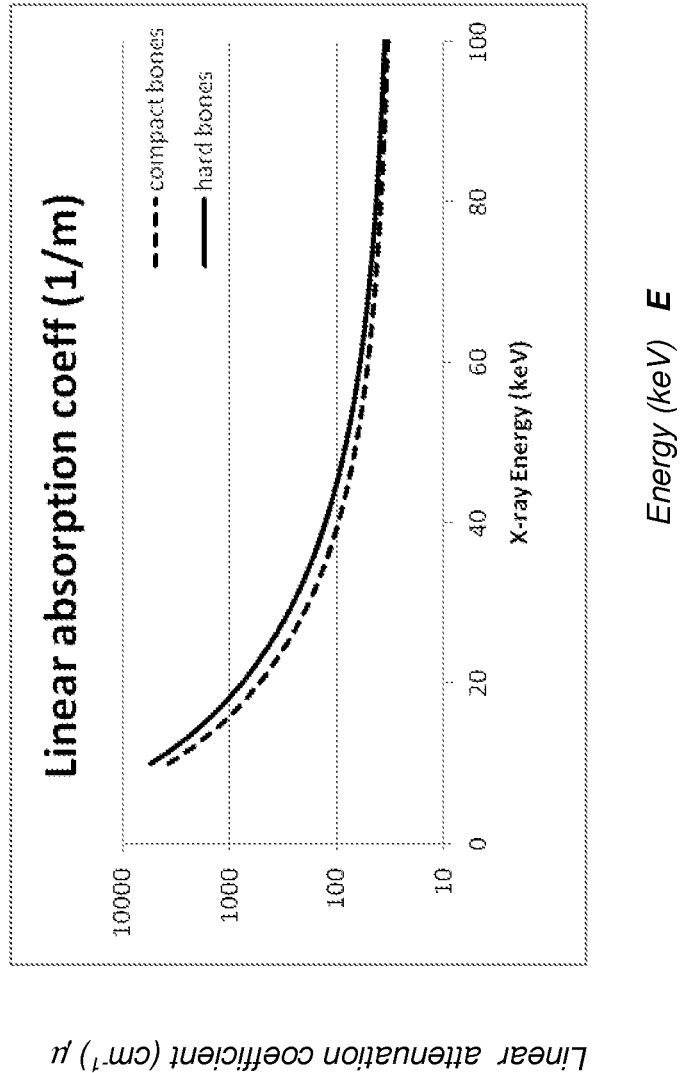
FIG. 6B is a graph that shows the linear absorption coefficient for different types of bone tissue.

The capability to count photons at different energy thresholds, as described with reference to FIG. 5, allows the sensor to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. As shown for typical metals in the simplified graph of FIG. 6A, two materials A and B have different coefficients of attenuation $\mu$ that vary with the level of radiation energy, shown as exposure E. At a given exposure, material A attenuates a photon with an energy that corresponds to material A, as shown at value A1. Similarly, radiation impinging on material B attenuates a photon with an energy that corresponds to material B, as shown at value B1. Where photons of these different energy values can be differentiated from each other, it is possible to identify one or both materials in the same pixel or voxel image element of the obtained image. This same basic behavior in response to radiation also allows some measure of capability to differentiate tissue types. By way of example, the graph of FIG. 6B shows relative coefficients of attenuation for different bone densities. As FIG. 6B suggests, different linear absorption characteristics allow differentiation between various types of tissue, such as between bone types.

Color x-ray using photon counting detectors provides for low cost and low dose color x-ray imaging. The use of multi-spectral or "color" x-ray imaging can have a number of potential benefits of value for dental, ENT, and head imaging. These include minimization of metal artifacts, separate reconstruction of soft and hard tissue, more efficient segmentation algorithms for tooth and bone features, improved pathology detection for cancer and other disease, and detection of trace materials or contrast agents.

In addition to opportunities for improvement in the image processing chain, there are a number of differences in structure, operation, scanning sequence, dimensions, and supporting hardware that are needed to provide the advantages of photon counting in embodiments of the present invention. As one significant difference from conventional large-area image detection, the photon-counting architecture results in an image detector of reduced size, generally requiring a scanning sequence even where only a 2-D image is obtained. For volumetric imaging, such as in the sequence needed for CT or for cone-beam CT (CBCT) imaging, it may be necessary not only to scan within the same plane, but to provide a 3-dimensional helical scan.

Figure 7:
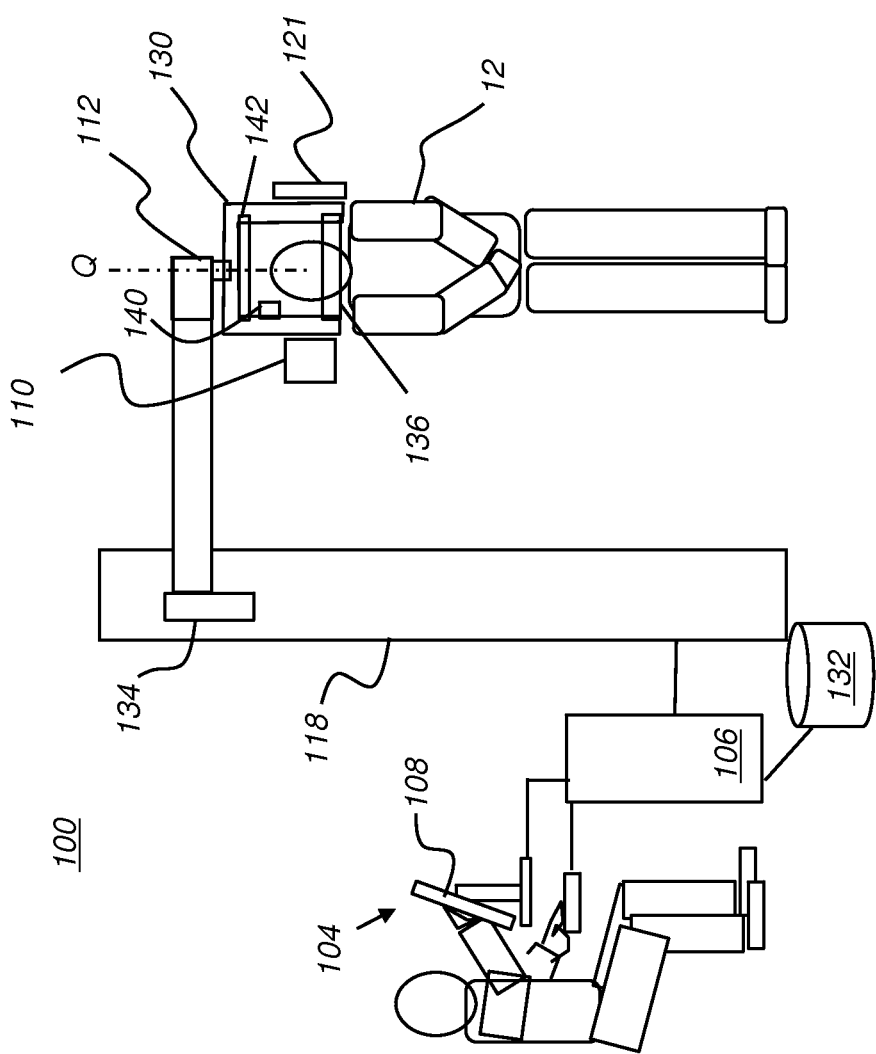
FIG. 7 is a schematic diagram showing an imaging apparatus for imaging portions of the patient's head using photon counting.

The schematic diagram of FIG. 7 shows an imaging apparatus 100 for 2-D imaging, such as panoramic imaging, in which a succession of two or more 2-D images is obtained and images of adjacent content are arranged to form a larger image, or for 3-D imaging, such as tomography, computed tomography volume imaging, or cone beam computed tomography (CBCT) imaging in dental, ENT, and related head imaging applications. A rotatable mount 130 is provided on a column 118, preferably adjustable in height to suit the size of patient 12. Mount 130 maintains x-ray source 110 and a radiation sensor 121 on opposite sides of the head of patient 12 and, optionally, rotates to orbit source 110 and sensor 121 in a scan pattern about the head. Mount 130 rotates about an axis Q that corresponds to a central portion of the patient's head, so that its attached components orbit about the head. Sensor 121, a photon-counting sensor according to an embodiment of the present invention, is coupled to mount 130, opposite x-ray source 110 that emits a radiation pattern suitable for 2-D imaging, for tomosynthesis imaging, or for CT or CBCT volume imaging. An optional head support 136, such as a chin rest or bite element, provides stabilization of the patient's head during image acquisition. A computer 106 has an operator interface 104 and a display 108 for accepting operator commands and for display of volume images obtained by imaging apparatus 100. Computer 106 is in signal communication with sensor 121 for obtaining image data and provides signals for control of source 110 and, optionally, for control of a rotational actuator 112 for mount 130 components. One or more height sensors 134 is also sensed by computer 106 in order to obtain an initial height setting and to track relative vertical displacement of the sensor 121 relative to the patient's head during the helical scan. Computer 106 is also in signal communication with a memory 132 for storing image data. An optional alignment apparatus 140 is provided to assist in proper alignment of the patient's head for the imaging process. Alignment apparatus 140 includes a laser that provides one or more line references for head positioning according to an embodiment of the present invention. In alternate embodiments, alignment apparatus 140 includes a visible light beam or other marker, or a mechanical or other positioning apparatus. Imaging apparatus 100 may also have the capability for panoramic or cephalometric imaging using x-ray source 110 and sensor 121 or other imaging sensor.

There can be a number of variable scan patterns according to the type of imaging that is required. Tomosynthesis, for example, typically uses a scan that is less than 180 degrees about the patient. CBCT scanning may require a helical scan pattern with one or more revolutions about the patient's head. An optional adjustment mechanism 142 is provided for adjusting the source-to-image (SID) distance between the x-ray source 110 and sensor 121 to suit the scan pattern for different patients or types of imaging.

One drawback of typical photon-counting image detectors is their relatively small size. Unlike a conventional digital radiography imaging panel that has an array with hundreds of elements in the height and width directions, the photon-counting sensor is typically of smaller size, with a width that may be fewer than 100 pixels in dimension. This problem can be addressed by tiling, an approach in which multiple image detectors are combined to cover a larger detection area. The use of polycrystalline materials, as opposed to conventional monocrystalline detector materials as noted earlier, can also help to provide larger detectors.

Figure 8:
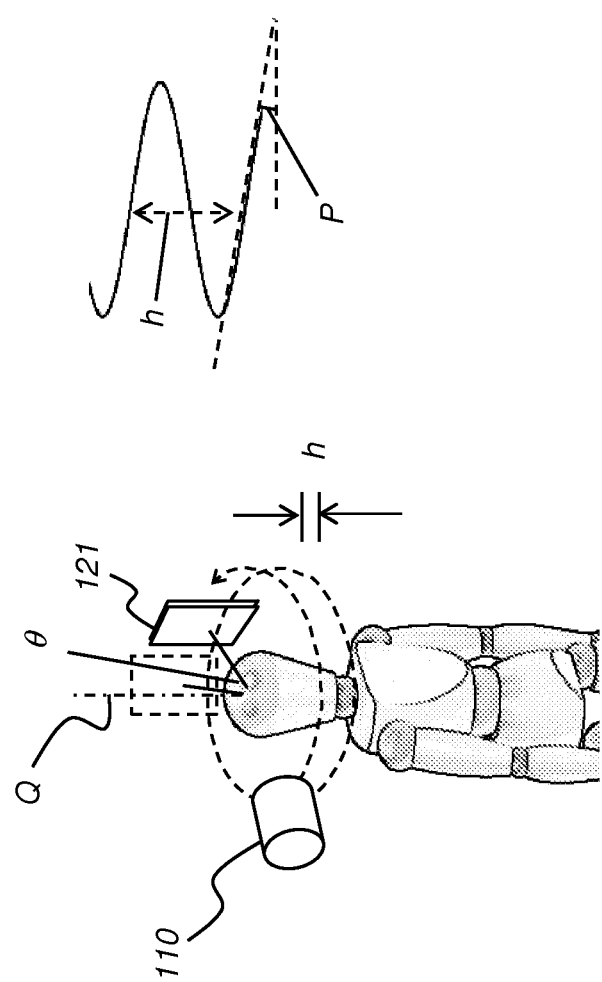
FIG. 8 is a schematic diagram that shows a portion of a helical scan for the digital sensor and radiation source.

Another solution for the size constraints of photon-counting image detectors adapts their scanning sequence to effectively increase the field of view. In practice, this size limitation requires a different scanning sequence from that used for conventional CBCT imaging. A helical scan can be used to acquire the needed image data for volume imaging. In operation, mount 130 rotates about the head of patient 12 multiple times, thereby scanning sensor 121 about patient 12 in a helical orbit, as is shown in FIG. 8. In FIG. 8, an adjacent imaging position is shown in dotted outline, with the angular distance exaggerated for clarity. According to an embodiment of the present invention, the vertical height h change of the helix during revolution of the source and detector, which can also be expressed in terms of the helical pitch angle P, and angular change θ between successive image acquisitions, is adjustable.

Figure 9A:
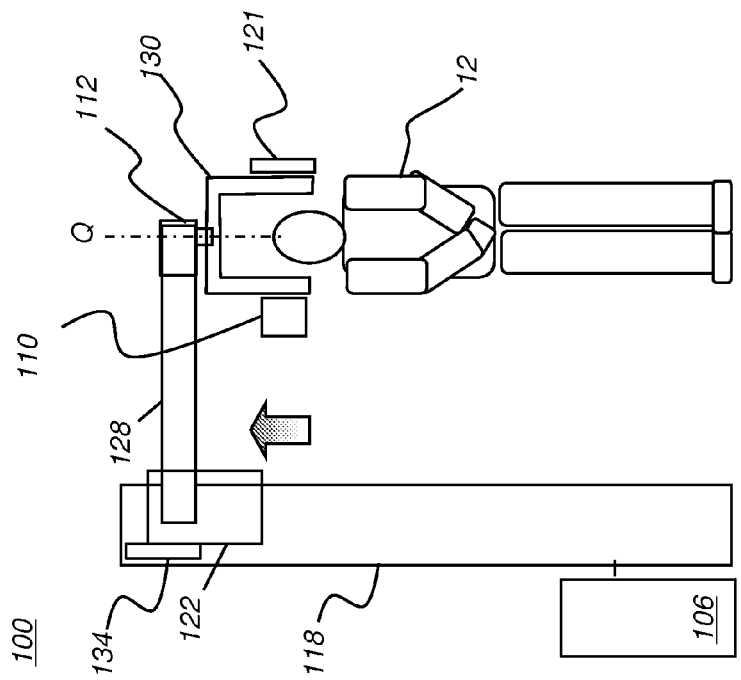
FIGS. 9A and 9B show the imaging apparatus that provides a helical scan by changing the elevation of a support arm during revolution about the patient.
Figure 9B:
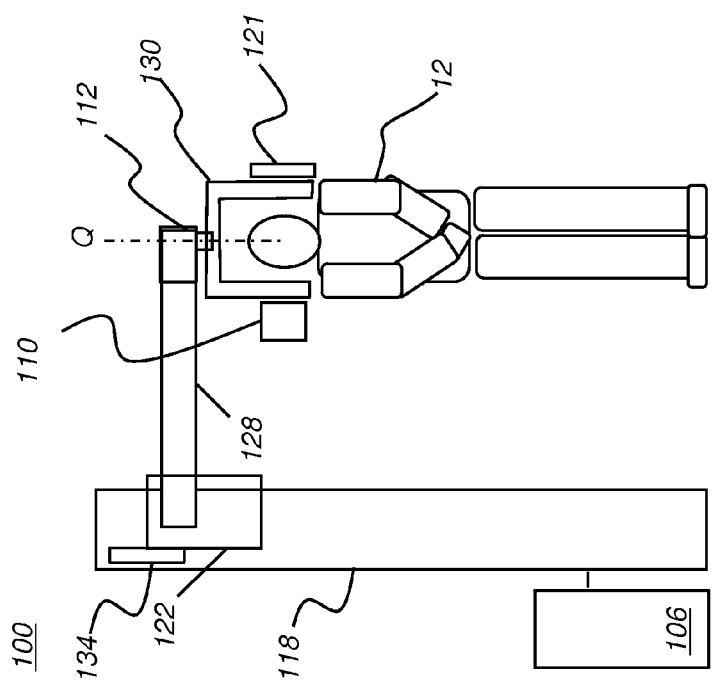

The helical scan needed for CBCT imaging using a photon-counting sensor 121 can be provided following either of a number of scanning apparatus models. FIGS. 9A and 9B show a first approach to this problem, in which mount 130 that contains sensor 121 and source 110 is itself coupled to a movable travel arm 128 that is vertically translated during the scan, displaced by an actuator 122 during rotation of mount 130. This translation changes the relative vertical position of the imaging sensor and the radiation source to the patient's head during the helical scan. In one embodiment for the helical scan, an imaging sensor can be a slit shaped sensor with the longest dimension configured to extend during the scan in a direction that is perpendicular to the helix axis.

Figure 10A:
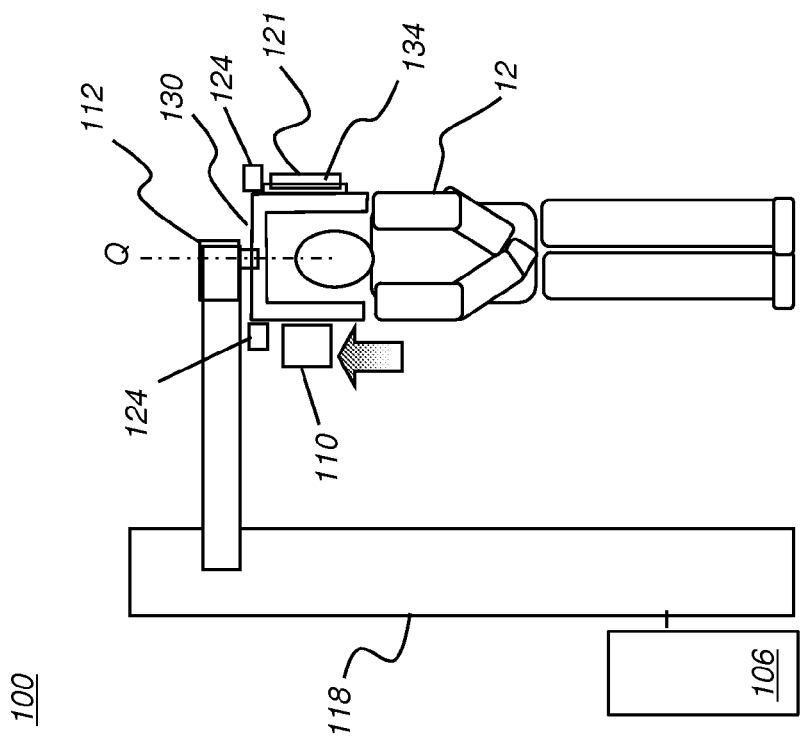
FIGS. 10A and 10B show the imaging apparatus that provides a helical scan by changing the elevation of the digital sensor and radiation source during revolution about the patient.
Figure 10B:
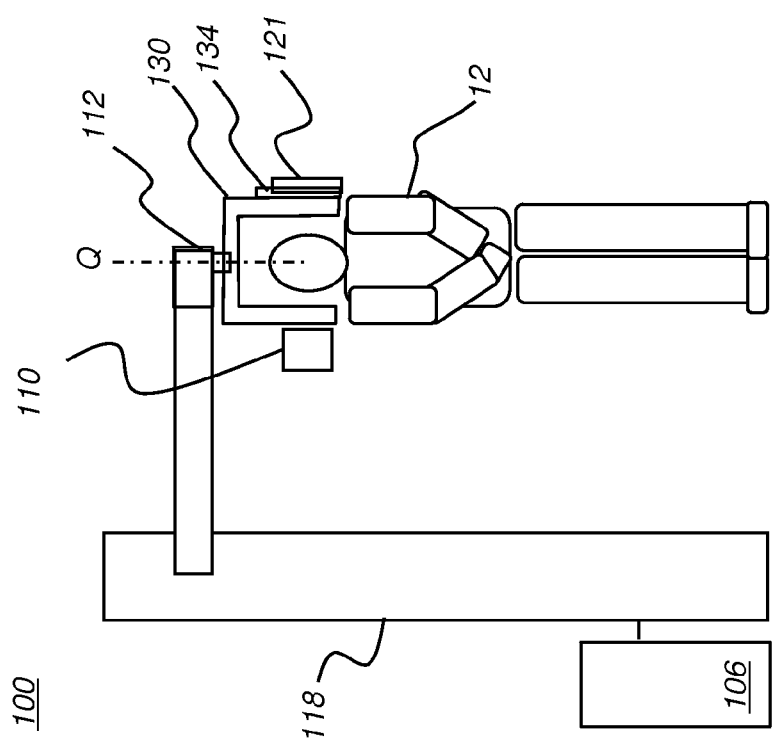
Figure 11A:
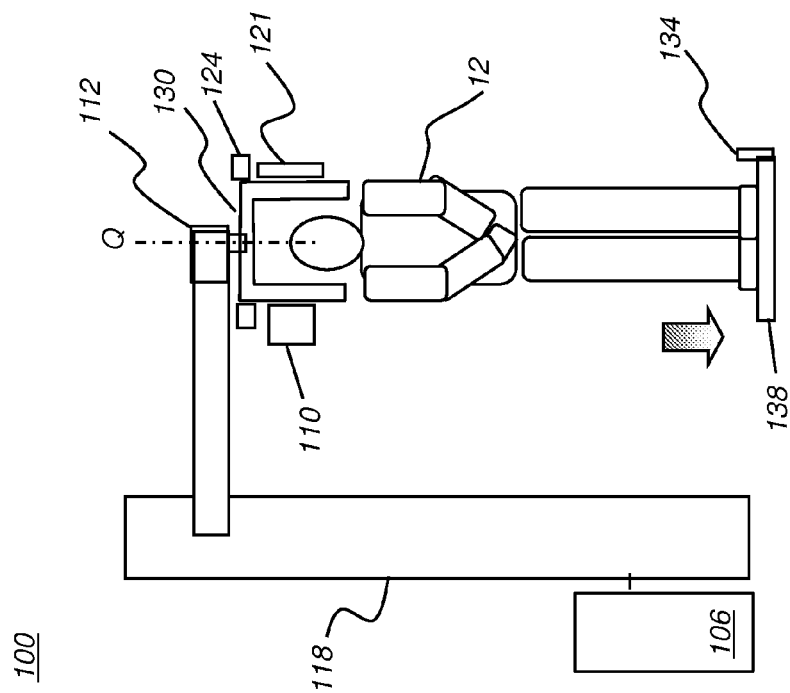
FIGS. 11A and 11B show the imaging apparatus that provides a helical scan by changing the elevation of the patient's head relative to the digital sensor and radiation source during revolution about the patient.
Figure 11B:
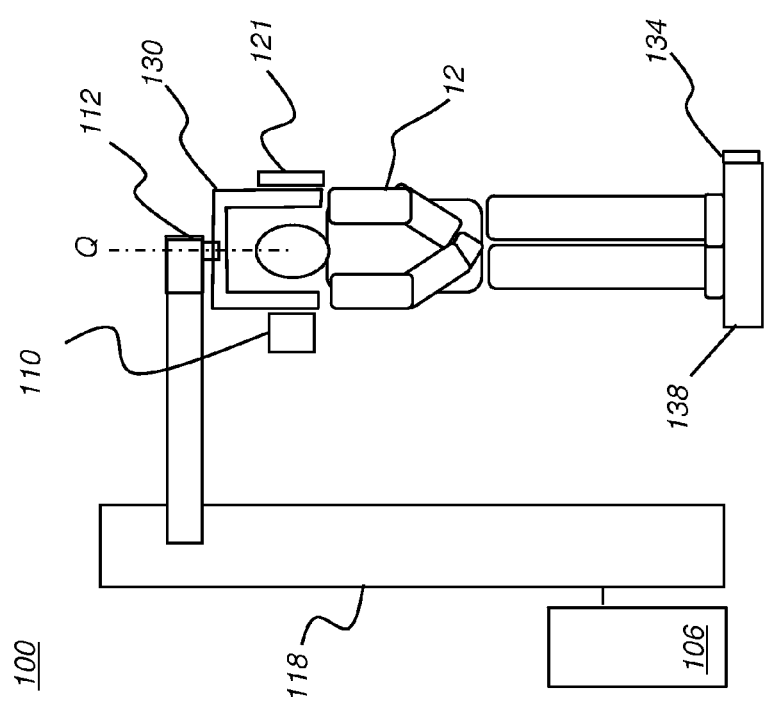

FIGS. 10A and 10B show a second approach to this problem, in which mount 130 itself has the same height, while source 110 and sensor 121 are vertically translated during the helical scan, thereby changing the relative vertical position of the imaging sensor and the radiation source to the patient's head during the helical scan. FIGS. 11A and 11B show a third approach to this problem, in which mount 130 itself has the same height, while a vertically adjustable platform 138 is used as an actuator to provide relative movement between the head of the patient and source 110 and sensor 121 for changing the relative vertical position of the imaging sensor and the radiation source to the patient's head during the helical scan.

As shown in FIGS. 9A-11B, one or more actuators 124 within mount 130, or other height adjustment devices provide this vertical translation function as source 110 and sensor 121 revolve about the patient's head. Computer 106 coordinates and tracks the vertical and rotational or angular movement and corresponding actuators needed for helical scanning. Sensor 134 provides feedback information on height with the FIG. 9A/B, FIG. 10A/B and FIG. 11A/B scan configurations.

Operation Sequence

Figure 12:
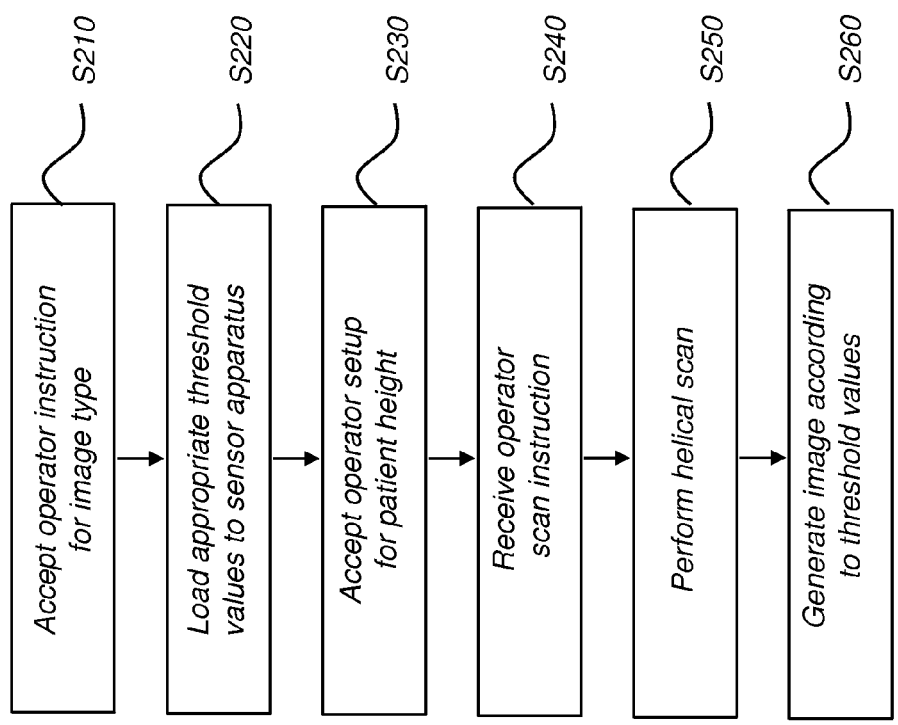
FIG. 12 is a logic flow diagram showing steps for image acquisition according to an embodiment of the present invention.

The logic flow diagram of FIG. 12 shows an operational sequence for CBCT scanning of the head according to an embodiment of the present invention, for the imaging apparatus shown in FIGS. 7, 9A, 9B, 10A, 10B, 11A, and 11B. In an accept instruction step S210, the imaging apparatus accepts operator instructions related to the type of image to be obtained, which may include information on the types of tissue that are of particular interest. In a threshold setup step S220 an appropriate set of threshold values and other operational parameters is loaded to circuitry of sensor 121. An operator setup step S230 allows the operator to adjust mount 130 components to suit the height of the patient and size of the patient's head. This registers an initial height setting that provides information for subsequent helical scan execution. The operator can also use head support 136 and alignment apparatus 140 to adjust patient position. An instruction entry step S240 accepts the operator instruction to begin the scan sequence and to execute a scan and acquisition step S250. During step S250, multiple 2-D images are obtained at successive rotational and height positions for acquiring the CBCT scan data. An image generation step S260 then forms the 3-D volume image from the obtained 2-D images, using an image reconstruction algorithm, such as one of the filtered back-projection routines well known in the volume imaging arts. The resulting image is then displayed for viewing by the practitioner and the image data is stored in memory 132 (FIG. 7) or other memory circuitry that is accessible to computer 106.

According to an embodiment of the present invention, the tissue type of interest dictates the set of operational parameters that are most suitable for imaging a particular patient. By way of example, and not by way of limitation, Table 1 lists a set of parameters that are loaded when the operator elects to generate an image for tissue type A. Table 2 lists alternate example parameters for generating an image for tissue type B. As described earlier with respect to FIG. 8, the pitch of the helical scan pattern can be specified in terms of vertical translation or helical pitch angle P. The helical pitch angle P can be varied from 0 degrees (that is, a slope of 0) to 40 degrees or more and is based on the relative size of the sensor 121 and the amount of overlap needed between successive images.

It can be appreciated that some modification of procedures listed and described with reference to FIG. 12 are similarly used for other types of imaging using imaging apparatus 100, with appropriate changes for the scan pattern and number of images obtained. For panoramic or tomosynthesis imaging, for example, a full scan is not needed. Only a partial scan is needed, with the scan orbit defined within a single plane, rather than helical as described for CBCT scanning.

TABLE 1

Operational Parameters for Tissue Type A

| Parameter | Setting |
| --- | --- |
| Radiation energy level | 30 kVp |
| Threshold values to sensor | +1.23 V |
|  | +1.41 V |
| Image acquisition interval | every 0.8 degrees |
| Vertical translation between images | 0.1 mm |

TABLE 2

Operational Parameters for Tissue Type B

| Parameter | Setting |
| --- | --- |
| Radiation energy level | 40 kVp |
| Threshold values to sensor | +1.02 V |
|  | +1.34 V |
| Image acquisition interval | every 0.9 degrees |
| Vertical translation between images | 0.12 mm |

As noted earlier with respect to FIG. 5, different types of materials have different photon energy "signatures", enabling the volume scan to detect two or more different materials in the imaged subject. This feature enables the same imaging apparatus to be employed for obtaining different information using the same scanning pattern. According to an embodiment of the present invention, different sets of threshold settings are provided, depending on the nature of the volume image that is desired. One set of threshold settings, for example, is optimized for obtaining information on teeth, while another set of threshold settings works best for imaging gum and underlying support structures. Still another set of threshold settings provides the best conditions for imaging of the throat, ear, or nasal passages, with corresponding elevation adjustments. As described with reference to FIG. 12, an appropriate set of threshold values is selected and loaded to the image acquisition circuitry of the imaging sensor according to the type of imaging that is to be performed and to the type of tissue that is of particular interest for a patient.

Embodiments of the present invention have been described for imaging various regions of the head and upper body of a patient using an extra-oral detector. The apparatus of the present invention can be used, for example, to obtain a full-mouth series (FMS) in dental practice. It should be noted that sensor 121 (FIG. 7) can combine photo-counting circuitry with other, conventional imaging components, such as with indirect detection or integrating imaging components described earlier with reference to FIGS. 2A-D. Multiple sensors 121 can be coupled together to increase the area over which an image is obtained for each x-ray exposure. The photon-counting sensor 121 can be used to support different imaging modes, including CT or CBCT, panoramic, or cephalometeric imaging. CT and CBCT imaging modes obtain a volume image from multiple 2-dimensional (2-D) images. Panoramic and cephalometeric imaging are 2-dimensional imaging modes that may require scanning of sensor 121 in one or two directions within the same imaging plane during imaging in order to cover the full imaging area.

With the necessary adaptations to hardware and to the scanning patterns that are used, embodiments of imaging apparatus 100 (FIG. 7) are capable of a number of types of imaging, including 2-D imaging and panoramic imaging, tomosynthesis imaging, and volume imaging using computed tomography (CT) or cone-beam computed tomography (CBCT).

Tomosynthesis is an imaging type that takes advantage of the capability of systems such as imaging apparatus 100 to localize focus over some portion of an arc and to process the resulting image data in order to provide an image that provides some amount of depth information from a series of individual 2-D images obtained at different angles along the arc. Tomosynthesis thus provides a type of volume image, formed from a sequence of two-dimensional (2-D) images. Basic principles for dental tomosynthesis are described, for example, in U.S. Pat. No. 5,677,940.

Figure 13:
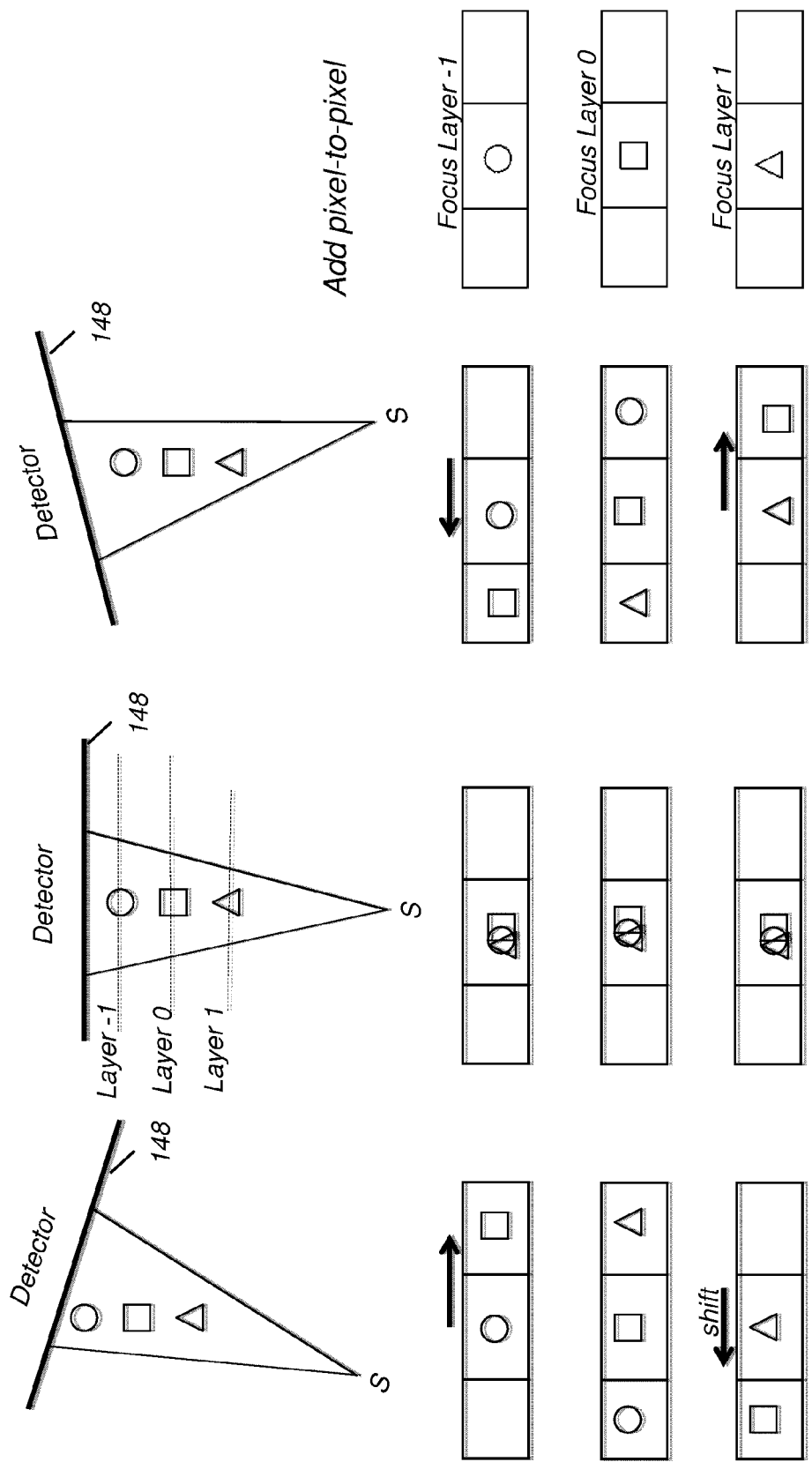
FIG. 13 is a schematic diagram that shows features of image acquisition and processing for tomosynthesis according to an embodiment of the present invention.
Figure 14:
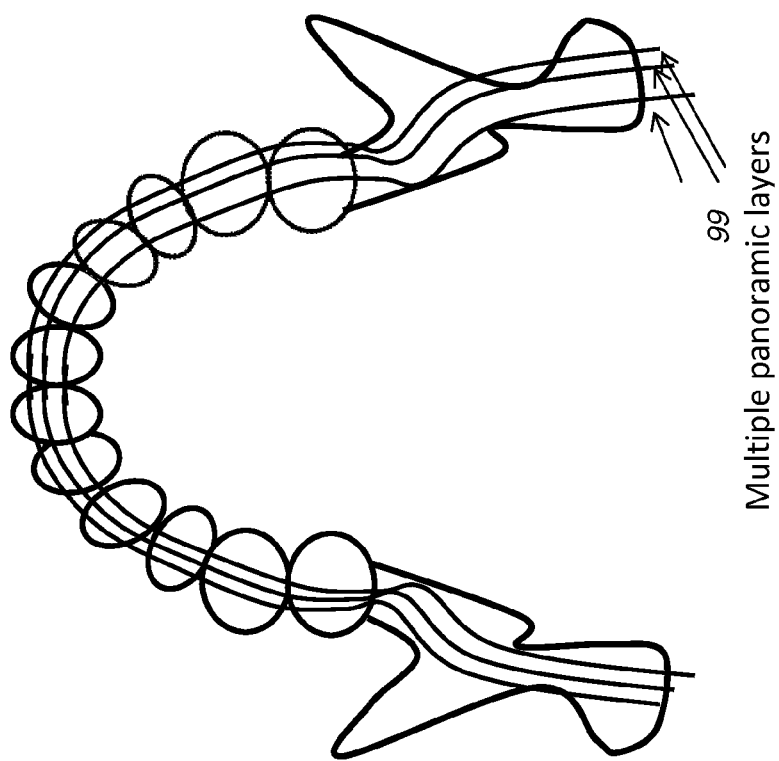
FIG. 14 is a top view diagram that shows example panoramic layers within the dental arch for a patient.

The schematic diagram of FIG. 13 shows how tomosynthesis operates to obtain images at different focus layers. Radiation from a source S is directed through an object, shown in FIG. 13 as one of a set of geometric shapes in different focal planes, to a detector 148. Layers are indicated as layer −1, layer 0, and layer 1. Source S or detector 148 travel in an arc, as shown during image acquisition. Images on one tomosynthesis plane or layer are combined with corresponding images in the sequence with objects in images from other tomosynthesis layers, such as by straightforward addition of pixels, in order to provide a combined volume image. As the radiation source and sensor are positioned on opposite sides of the patient's head, a number of bony structures are superimposed within the individual 2-D images that are obtained. For example, it can be difficult to differentiate incisors from spine or molars from other structures along the dental arch, as shown in FIG. 14. Superimposed images used for tomosynthesis, with successive images obtained at different angles, allow reconstruction of the underlying features and retrieval and representation of the proper depth information. This technique allows obtaining a best focus layer at a preset position and with a preset speed profile and collimation setting. As pixels are added in combination, bony structures lying outside of the layer of best focus tend to blur, without degrading the visualization of bony structures that lie within the region of interest. By way of example, FIG. 14 shows multiple panoramic layers 99 along the dental arch.

One drawback of this technique relates to the discrepancy that can occur between the focus layer and the actual region of interest, such as the patient's teeth. This can occur even when the locus of the rotation axis is predefined for a given region along the dental arch or other structure. However, this disadvantage can be remedied by permitting the choice of a best focus layer that is different from the preset layer and by adapting the position of this best focus layer relative to the shape of the patient's dental arch. In processing, a shift of pixels within each image is performed, the amplitude of the shift chosen so that the position of the anatomical structure of interest is located, after shifting, at the same position on each image. After a pixel-to-pixel adding process of the plurality of acquired images, a final image is obtained in which the anatomical structure of interest is located in the focus layer and other structures are blurred (resulting in horizontal stripes, for example). By repeating the process with other shift amplitudes values, a plurality of focus layers can be obtained and the best one can be chosen for a region of interest. Among advantages of this technique can be image quality, which is only slightly dependent upon the positioning of the patient.

In alternate exemplary embodiments, a photon-counting sensor is used as an intraoral sensor. It can be appreciated that a number of modifications to related art photon counting sensors are required for this purpose. One difficulty relates to resolution requirements for intraoral imaging. Extraoral imaging sensors have relatively large pixel sizes compared with pixel sizes for the resolution needed for intraoral imaging. Typical pixel sizes for extraoral imaging sensors can be on the order of 100 microns or more; intra-oral imaging requires resolution on the order of 20 microns or less. At the same time, 8-bit or better depth resolution is needed, requiring considerable support circuitry for digital counters associated with each pixel. To address the need for higher resolution and/or sufficient bit depth for intraoral dental imaging, exemplary embodiments herein can employ an alternate methods/apparatus for counting photon events, by using an analog photon counting device (e.g., analog charge storage device) to reduce support circuitry included in the digital counters associated with each pixel. In one embodiment, the support circuitry (e.g., transistors) can be reduced by a factor of 2×, 5× or 10×. For each radiation photon (e.g., x-ray) that is received, the resulting electron cloud can generate a pulse or cause a charge (e.g., preset charge) to be stored in a capacitor or other analog storage device. In one embodiment, a lower threshold can be used to reduce or eliminate storing charge in the capacitor for noise or erroneous events (e.g., scatter). Over time, the amount of charge (that is, current, voltage) that is stored in the analog storage device is indicative of the number of photons received for the corresponding pixel. For example, analog-to-digital circuitry senses the stored charge and provides an output digital value that indicates the photon count for the pixel. In one embodiment, a plurality of analog photon counting devices can be provided for each imaging pixel to support a plurality of thresholds to implement pulse counts for a number of threshold values even for the reduced imaging pixel size of the intra-oral digital sensor.

Other changes for intraoral use include thinning of direct detection element 72 (FIG. 3). This helps to reduce the amount of radiation needed and/or allows lower voltage levels to be used to attract the electron cloud toward energy detecting elements 54. At the same time, radiation-hardening can be used needed to help protect energy detecting elements 54 that sense the resulting electron cloud from direct detection element 72. In addition, because some photons can escape without interaction with direct detection element 72, the use of an additional upper threshold can reduce or alleviate noise effects from these photons. A voltage condition (e.g., transient) above this upper threshold is thus not counted. Both lower and upper threshold conditions can be used to effectively validate the photon count. The lower threshold can reduce noise effects; the upper threshold can reduce the effects of radiation (e.g., photons) directly on detector circuitry. In one embodiment, a plurality of thresholds can be implemented in between the lower threshold and the upper threshold to provide detection of materials of different characteristics in the head of the patient. For example, the plurality of thresholds can be used to differentiate soft tissue and bone, and/or to identify and remove or reduce metal artifacts in the dental imaging system diagnostic image of the patient. Additional lead shielding is also provided behind the intra-oral detector to reduce any stray radiation from passing through the detector.

In one exemplary embodiment for an analog photon counting device included in a digital counter, each energy cloud of electrons, which result from a radiation photon, received by an intraoral sensor imaging pixel can result in a pulse being generated by the intraoral sensor imaging pixel. The pulse can be used to increment a counter. Alternatively, the pulse can be used by the intraoral sensor imaging pixel to implement a preset electric charge that can be used for analog photon counting over the radiation interval. For example, the preset electric charge can be stored (e.g., integrated or counted) into an analog storage device for each pulse for each intraoral sensor imaging pixel during the radiation interval. Then, photon counting can be determined by dividing a total stored charge for the radiation interval in the analog storage device by the preset electric charge. Alternative embodiments for analog photon counting in the digital detectors for intraoral sensors can be used. Further, a plurality of analog photon counting devices can be included in a digital counter for each intraoral sensor imaging pixel to implement a plurality of thresholds or a plurality of ranges (e.g., a first threshold, a second threshold, a third threshold, responsive to a first range of photon energy, responsive to a second range of photon energy, etc.) to differentiate a plurality of materials in a dental diagnostic image or to implement low dose and/or multi-spectral or "color" x-ray imaging in dental intraoral photon counting direct sensor imaging systems/methods.

Intraoral applications using these photon counting detectors can be 2D intraoral imaging and 3D intraoral imaging. 2D intraoral imaging includes individual images of patient's teeth/mouth using an intraoral detector. 3D intraoral imaging includes multiple images of patient's teeth/mouth using an intraoral detector, and combining these images into 3D representation. This has been referred to as chair-side cone beam CT. Chair-side cone beam CT allows a dental practitioner to obtain a 3D image without moving/transporting a patient to a full 3D imaging station/equipment during a surgical procedure.

It should be noted that extra-oral embodiments of the present invention can also provide an analog count, rather than using a digital counter arrangement. The accumulated analog charge, incremented once for each photon, can be distinguished from conventional types of integrated radiation detection that provide a digital value according to the relative brightness of each pixel in the scintillator.

Consistent with an embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing processes and for recording entered values, such as seed points, or storing intermediate and final results of calculations and other processing. Computer-accessible memory can be volatile, non-volatile, or a hybrid combination of volatile and non-volatile types. Computer-accessible memory of various types is provided on different components throughout the system for storing or recording, processing, transferring, and displaying data, and for other functions.

A first example embodiment can provide a dental imaging apparatus for obtaining an image from a patient, the apparatus comprising a radiation source; a digital imaging sensor that provides, for each of a plurality of image pixels, at least a first digital value according to a count of received photons that exceeds at least a first energy threshold, wherein the imaging sensor comprises a direct-detection material that converts incident x-ray photons to an electron flow; a mount that supports at least the radiation source; and a computer in signal communication with the digital imaging sensor for acquiring one or more two-dimensional images. In one example, the dental imaging apparatus can be an extra-oral dental imaging apparatus or an intra-oral dental imaging apparatus. In one embodiment, the dental imaging apparatus can be an extra-oral dental imaging apparatus or an intra-oral dental imaging apparatus.

A second example embodiment can provide a dental imaging apparatus for obtaining an image from a patient, the apparatus comprising a radiation source; a digital imaging sensor that provides, for each of a plurality of image pixels, at least a first digital value according to a count of received photons that exceeds at least a first energy threshold, wherein the imaging sensor comprises mercuric iodine (e.g., HgI2) to convert incident x-ray photons to an electron flow; a mount that supports at least the radiation source; and a computer in signal communication with the digital imaging sensor for acquiring one or more two-dimensional images.

In one embodiment, the dental imaging apparatus can be an extra-oral dental imaging apparatus or an intra-oral dental imaging apparatus.

A third example embodiment can provide an intra-oral dental imaging apparatus for obtaining an image from a patient, the apparatus comprising a radiation source; a digital imaging sensor that provides, for each of a plurality of image pixels, at least a first digital value according to a count of received photons that satisfy at least a first energy threshold; and a computer in signal communication with the digital imaging sensor for acquiring one or more two-dimensional images. The intra-oral dental imaging apparatus can include an alignment system to align the radiation source to the digital imaging sensor, where the alignment system can be mechanical, electromechanical or optical. The intra-oral dental imaging apparatus can include a mount that supports the radiation source. The intra-oral dental imaging apparatus can include a second digital value according to a count of received photons that satisfy a second energy threshold for each of the plurality of image pixels.

A fourth example embodiment can provide an method of operating an intra-oral dental imaging system for obtaining image data of at least a portion of a patient's head, the method comprising providing a digital imaging sensor that provides, for each of a plurality of image pixels, at least a first digital value according to a count of received photons that satisfy at least a first energy threshold; obtaining a set of values that relate to one or more of an exposure energy level; orienting a radiation source to the digital imaging sensor; acquiring a plurality of digital images according to the obtained set of values; and generating and displaying a diagnostic image formed from the plurality of acquired digital images.

A fifth example embodiment can provide an imaging apparatus for obtaining a volume image of at least a portion of a patient's head, the apparatus comprising a rotatable mount comprising a radiation source and a digital imaging sensor and coupled to a rotational actuator that is energizable to revolve the imaging sensor and source in a scan pattern about the patient's head; and a computer in signal communication with the digital imaging sensor for acquiring a plurality of two-dimensional images at successive positions along the scan pattern; wherein the imaging sensor provides, for each of a plurality of image pixels, a digital value according to a count of received photons that exceed at least one energy threshold. The imaging apparatus can include one or more vertical actuators energizable for changing the relative vertical position of the imaging sensor and the radiation source to the patient's head during the revolution.

Example imaging apparatus embodiments can include polycrystalline materials or monocrystalline materials, wherein the polycrystalline materials or monocrystalline materials comprise cadmium telluride (CdTe or CadTel), lead iodine (PbI), lead oxide (PbO), and mercuric iodide (HgI2) for the digital imaging sensor.

Example imaging apparatus embodiments can include each imaging pixel configured to generate a pulse for each received photon that exceeded the at least one energy threshold, where a clock is incremented by the pulses.

Example imaging apparatus embodiments can include the imaging sensor configured to provide an upper threshold, wherein the each imaging pixel outputs a first pulse for a received photon that is above the first energy threshold and is less than the upper threshold, and wherein the each imaging pixel outputs a second pulse for a received photon that is above a second energy threshold and is less than the upper threshold, wherein a prescribed electric charge is generated for said each first and second pulse. Alternatively, a first photon counting is determined by dividing a first total electric charge responsive to the first pulses by a prescribed electric charge relative to one first pulse, and wherein a second photon counting is determined by dividing a second total electric charge responsive to the second pulses by a prescribed electric charge relative to one second pulse. In one embodiment, the first and second pulses are mutually exclusive.

The invention has been described in detail with particular reference to a presently preferred embodiment, but it will be understood that variations and modifications can be effected within the spirit and scope of the invention. For example, sensor 121 can be a photon-counting sensor or an integrating image sensor. In addition, while a particular feature of the invention can have been disclosed with respect to at least one of several implementations/embodiments, such feature can be combined with one or more other features of the other implementations/embodiments as can be desired and advantageous for any given or particular function. The term "at least one of" is used to mean one or more of the listed items can be selected. "Exemplary" indicates the description is used as an example, rather than implying that it is an ideal. The presently disclosed embodiments are therefore considered in all respects to be illustrative and not restrictive.

The invention claimed is:

1. A dental imaging apparatus for obtaining an image from a patient, the apparatus comprising:
   a radiation source;
   a digital imaging sensor that provides, for each of a plurality of image pixels, a first lowest energy value according to a count of received photons of ionizing radiation energy that exceed at least a first lowest energy value threshold;
   a mount that supports the radiation source in a spaced relationship relative to the digital imaging sensor with respect to the patient's head;
   and
   a computer in signal communication with the digital imaging sensor for acquiring one or more two-dimensional images,
   wherein the digital imaging sensor further provides, for each of the plurality of image pixels, a second highest energy value obtained from a count of photons of ionizing radiation energy that exceed a second highest energy value threshold that is greater than the first lowest energy value threshold, wherein the imaging sensor further provides an upper threshold that is greater than the second highest energy value threshold, wherein the first lowest energy value is according to the count of received photons of ionizing radiation energy that both exceeds the first lowest energy value threshold and are less than the upper threshold, and wherein the second highest energy value is according to the count of received photons of ionizing radiation energy that both exceed the second highest energy value threshold and are less than the upper threshold, and
   where an image of at least a part of the patient's head is reconstructed using only the first lowest energy value and the second highest energy value for the plurality of image pixels.

2. The apparatus of claim 1 wherein the mount is coupled to a rotational actuator that is energizable to revolve the imaging sensor and source in a scan pattern about the patient's head, wherein a volume image of at least a part of the patient's head is reconstructed based on the plurality of image pixels.

3. The apparatus of claim 2 further comprising one or more vertical actuators energizable for changing the relative vertical position of the imaging sensor and the radiation source to the patient's head and wherein the computer combines two or more images in the series to form a helical computed tomography volume image.

4. The imaging apparatus of claim 3 wherein the one or more vertical actuators translate the mount for changing the relative vertical position of the imaging sensor and the radiation source to the patient's head during imaging.

5. The imaging apparatus of claim 3 wherein the one or more vertical actuators translate the patient for changing the relative vertical position of the imaging sensor and the radiation source to the patient's head during imaging.

6. The imaging apparatus of claim 3 wherein the one or more vertical actuators change the relative vertical position of the imaging sensor and the radiation source to the patient's head at a variable rate.

7. The apparatus of claim 1 wherein the sensor is a two-dimensional sensor, and wherein the sensor and radiation source follow a trajectory in plane about a patient's head.

8. The imaging apparatus of claim 1 further comprising an alignment apparatus to provide alignment of the patient's head for obtaining the one or more images or at least one height sensor in communication with the computer.

9. The imaging apparatus of claim 1 wherein the mount is coupled to a rotational actuator that is energizable to revolve the imaging sensor and source in a scan pattern about the patient's head, wherein a two-dimensional image of at least a part of the patient's head is reconstructed based on the plurality of image pixels.

10. The imaging apparatus of claim 9 wherein the two-dimensional image is a panoramic image of a portion of the patient or the two-dimensional image is generated using tomosynthesis imaging techniques.

11. The imaging apparatus of claim 1 wherein the first lowest energy value threshold is selectable, and wherein the sensor is a direct imaging sensor.

12. The imaging apparatus of claim 1 where data from the imaging sensor corresponding to photons of ionizing radiation energy below the first lowest energy value threshold and above the upper threshold are not used in the image.

13. A method for obtaining volume image data of at least a portion of a patient's head, the method comprising:
   obtaining a set of values that relate to one or more of an exposure energy level and a scanning pattern;
   scanning a radiation source and a digital detector in a orbit about the patient's head according to the obtained set of values;
   acquiring a plurality of digital images at intervals in the scan according to the scanning pattern by providing for each of a plurality of image pixels in the plurality of digital images, a first lowest energy value according to a count of received photons of ionizing radiation energy that exceed a first lowest energy value threshold, a second highest energy value according to a count of received photons of ionizing radiation energy that both exceed a second highest energy value threshold and are below an upper energy threshold that is greater than the second highest energy value threshold, and discarding values from received photons of ionizing radiation energy both above the upper energy threshold and below the first lowest energy value threshold; and
   generating and displaying a image formed from the plurality of acquired digital images.

14. The method of claim 13 wherein obtaining the set of values comprises obtaining values entered by an operator relating to two or more exposure energy levels, wherein registering the initial setting is performed in response to an operator, and wherein scanning in the orbit allows a variable height between successive images and a variable pitch angle of revolution relative to the patient's head, according to a selected tissue type.

15. The method of claim 13, where the acquiring further comprises:
   at least one third middle energy value according to the count of received photons of ionizing radiation energy that both exceed a corresponding third middle energy value threshold and are less than the upper energy threshold, where any third middle energy value threshold lies between the first lowest energy value threshold and the second highest energy value threshold.

16. The apparatus of claim 1, where values from photons of ionizing radiation energy above the upper threshold are not used in the image.

17. The apparatus of claim 1, further comprising:
   at least one third middle energy value according to the count of received photons of ionizing radiation energy that both exceed a corresponding third middle energy value threshold and are less than the upper threshold, where any third middle energy value threshold lies between the first lowest energy value threshold and the second highest energy value threshold.

* * * * *